(12) United States Patent
Hong et al.

(10) Patent No.: US 11,568,538 B2
(45) Date of Patent: Jan. 31, 2023

(54) MEDICAL IMAGE-BASED TUMOR DETECTION AND DIAGNOSTIC DEVICE

(71) Applicant: Heuron Co., Ltd., Incheon (KR)

(72) Inventors: Jisu Hong, Incheon (KR); Soohwa Song, Incheon (KR)

(73) Assignee: Heuron Co., Ltd., Incheon (KR)

( * ) Notice: Subject to any disclaimer, the term of this patent is extended or adjusted under 35 U.S.C. 154(b) by 0 days.

(21) Appl. No.: 17/344,019

(22) Filed: Jun. 10, 2021

(65) Prior Publication Data

US 2022/0335599 A1 Oct. 20, 2022

(30) Foreign Application Priority Data

Apr. 16, 2021 (KR) .......................... 10-2021-0049901

(51) Int. Cl.
*A61B 5/00* (2006.01)
*G06T 7/00* (2017.01)
(Continued)

(52) U.S. Cl.
CPC ............ *G06T 7/0012* (2013.01); *A61B 5/004* (2013.01); *A61B 5/0042* (2013.01); *A61B 5/055* (2013.01);
(Continued)

(58) Field of Classification Search
CPC combination set(s) only.
See application file for complete search history.

(56) References Cited

U.S. PATENT DOCUMENTS

| 2016/0110904 A1* | 4/2016 | Jeon | A61B 5/4076 382/131 |
| 2018/0253622 A1* | 9/2018 | Chen | G06V 10/82 |

(Continued)

FOREIGN PATENT DOCUMENTS

| CN | 111833359 A | 10/2020 |
| JP | 7-284090 A | 10/1995 |

(Continued)

OTHER PUBLICATIONS

Hengxin Liu et al., "A Deep-Learning Model with Learnable Group Convolution and Deep Supervision for Brain Tumor Segmentation", Hindawi Mathematical Problems in Engineering, Feb. 10, 2021, vol. 2021, Article ID 6661083, pp. 1-11 (11 pages total).

(Continued)

*Primary Examiner* — Joel F Brutus
(74) *Attorney, Agent, or Firm* — Sughrue Mion, PLLC

(57) ABSTRACT

A device and a method for detecting a tumor using a medical image and diagnosing a shape and a property of the detected tumor are disclosed. An exemplary medical image-based tumor detection and diagnostic device includes: an input unit configured to obtain a medical image related to a patient; a preprocessing unit configured to preprocess the obtained medical image to observe a tumor region; an analysis unit configured to divide the preprocessed image into a plurality of regions by applying a deep neural network-based deep learning technique; and a measurement unit configured to group the plurality of divided regions by performing clustering on the plurality of divided regions. The measurement unit extracts a group feature value in respect to each of the grouped regions and derives diagnosis information related to the tumor based on the extracted group feature value.

10 Claims, 13 Drawing Sheets

(51) Int. Cl.
  *A61B 5/055* (2006.01)
  *G06N 3/04* (2006.01)
  *G06N 3/08* (2006.01)
(52) U.S. Cl.
  CPC ............ *A61B 5/7264* (2013.01); *G06N 3/04* (2013.01); *G06N 3/08* (2013.01); *G06T 2207/20021* (2013.01); *G06T 2207/20081* (2013.01); *G06T 2207/20084* (2013.01); *G06T 2207/30016* (2013.01); *G06T 2207/30061* (2013.01); *G06T 2207/30096* (2013.01)

(56) References Cited

U.S. PATENT DOCUMENTS

| | | | | |
|---|---|---|---|---|
| 2018/0308234 | A1* | 10/2018 | Chen | G16H 50/30 |
| 2019/0114511 | A1* | 4/2019 | Gao | G06N 7/005 |
| 2019/0362522 | A1* | 11/2019 | Han | A61B 5/0035 |
| 2020/0336699 | A1* | 10/2020 | Kim | G06N 3/08 |

FOREIGN PATENT DOCUMENTS

| | | |
|---|---|---|
| KR | 10-1284388 B1 | 7/2013 |
| KR | 10-1793609 B1 | 11/2017 |
| KR | 10-1919866 B1 | 11/2018 |
| KR | 10-2072476 B1 | 2/2020 |
| KR | 10-2100699 B1 | 4/2020 |
| KR | 10-2155381 B1 | 9/2020 |

OTHER PUBLICATIONS

Pius Kwao Gadosey et al., "SD-UNet: Stripping Down U-Net for Segmentation of Biomedical Images on Platforms with Low Computational Budgets", Diagnostics, Feb. 18, 2020, vol. 10, No. 110, pp. 1-18 (18 pages total).
Ramy A. Zeineldin et al., "DeepSeg: Deep Neural Network Framework for Automatic Brain Tumor Segmentation Using Magnetic Resonance FLAIR Images", International Journal of Computer Assisted Radiology and Surgery, May 5, 2020, vol. 15, pp. 909-920 (12 pages total).
Jeffrey D. Rudie et al., "Multi-Disease Segmentation of Gliomas and White Matter Hyperintensities in the BraTS Data Using a 3D Convolutional Neural Network", Frontiers in Computational Neuroscience, Dec. 20, 2019, vol. 13, Article 84, pp. 1-9 (9 pages total).
Office Action dated Mar. 15, 2022 issued by the Japanese Patent Office in Japanese Application No. 2021-095563.
Sunil L. Bangare et al., "Implementing Tumor Detection and Area Calculation in Mri Image of Human Brain Using Image Processing Techniques", Int. Journal of Engineering Research and Applications, 2015, vol. 5, No. 4, pp. 60-65 (6 pages total).
Manimuruga Shanmuganathan et al., "Review of advanced computational approaches on multiple sclerosis segmentation and classification", IET Signal Processing, Apr. 28, 2020, vol. 14, No. 6, pp. 333-341 (9 Pages total).
Muhammad Naeem Tahir, "Classification and characterization of brain tumor MRI by using gray scaled segmentation and DNN", Master's thesis, May 2018, Information Technology, Tampere University of Applied Sciences, pp. 1-46 (46 pages total).
Zhezhi He et al., "Sparse BD-Net: A Multiplication-less DNN with Sparse Binarized Depth-wise Separable Convolution", ACM Journal on Emerging Technologies in Computing Systems, Jan. 2020, vol. 16, No. 2, pp. 15:1-15:24 (24 pages total).
Abdul Qayyum et al., " Automatic Segmentation Using a Hybrid Dense Network Integrated With an 3D-Atrous Spatial Pyramid Pooling Module for Computed Tomography (CT) Imaging", IEEE Access, Digital Object Identifier, Sep. 15, 2020, vol. 8, pp. 169794-169803 (10 pages total).
Office Action dated Jul. 28, 2022 in European Application No. 21178472.3.
Extended European Search Report dated Dec. 7, 2021 in European Application No. 21178472.3.
Safia Fatima et al., "Evaluation of Multi-Modal MRI Images for Brain Tumor Segmentation"; 2019 15th International Conference on Emerging Technologies (ICET), IEEE, Dec. 2, 2019 (Dec. 2, 2019), pp. 1-6, XP033714041 (6 pages total).
Roy Choudhury Ahana et al: "Segmentation of Brain Tumors Using DeepLabv3+", Jan. 26, 2019 (Jan. 26, 2019), Advances in Databases and Information Systems; [Lecture Notes in Computer Science; Lect. Notes Computer], Springer International Publishing, CHAM, pp. 154-167, XP047502355 (14 pages total).

* cited by examiner

MEDICAL IMAGE-BASED TUMOR DETECTION AND DIAGNOSTIC DEVICE

CROSS-REFERENCE TO RELATED APPLICATIONS

This application claims the priority of Korean Patent Application No. 10-2021-0049901 filed on Apr. 16, 2021, in the Korean Intellectual Property Office, the disclosure of which is incorporated herein by reference.

BACKGROUND

Field

The present disclosure relates to a device and a method for detecting a tumor using a medical image and diagnosing a shape and a property of the detected tumor. More particularly, the present disclosure relates to a device and a method for detecting a tumor by adopting artificial intelligence (AI) based on medical imaging and patient information, diagnosing a shape and a property of the detected tumor, and providing information on prognosis prediction, thereby providing information suitable to allow a medical practitioner to diagnose a patient and establish a treatment plan.

Description of the Related Art

A tumor refers to a cell in a human body that has excessively grown with autonomy.

The growth of the tumor is always made by proliferation of tumor cells, and the types of growth of the tumor are broadly classified into two types and considered as important clinical factors that divide characteristics of tumors into benign tumors and malignant tumors.

One of the two types of growth of tumors is expansive or compressive growth, and the expansive or compressive growth can be found in the benign tumor. The other type of growth is infiltrative growth, and the infiltrative growth can be found in the malignant tumor. In the expansive growth, the tumor tissue grows as one group while pushing out peripheral normal tissue, and the expansive growth rarely causing direct damage. In the infiltrative growth, the tumor cell grows and infiltrates between peripheral tissue cells while destroying peripheral tissue, and the growth rate of the tumor is high.

Meanwhile, the states in which the tumor spread may be classified into two types. That is, there are a continuous spreading type and a discontinuous spreading type. In the continuous spreading type, the tumor continuously spreads around the primary site, and the expansive growth and the infiltrative growth belong to the continuous spreading type.

In the discontinuous spreading type, the tumor is moved from the primary site and then grows at a location spaced apart from the primary site, and the representative discontinuous spreading type is a metastasis.

The metastasis of the tumor is one of characteristics of the malignant tumor, and there are a lymphogenous metastasis and a hematogenous metastasis. In addition, there are the dissemination in which tumor cells are attached to the coelom and grow in large quantity at once, and the contact metastasis caused by contact.

In terms of maturity, the tumors can be classified into a mature tumor and an immature tumor. The mature tumor is the benign tumor, and the immature tumor is the malignant tumor. The tumors can be classified into an epithelial tumor and a non-epithelial tumor. In the case of the malignant tumor, the epithelial tumor is a carcinoma, and the non-epithelial tumor is a sarcoma.

Examples of the mature epithelial tumors include a papilloma, an adenoma, and a cystoma. Examples of the mature non-epithelial tumors include a fibroma, a myxoma, a lipoma, an osteoma, a melanoma, and a myoma. Further, examples of the immature epithelial tumors include a simple carcinoma, a squamous cell carcinoma, a cylindrical epithelial carcinoma, an adrenal tumor, a liver tumor, and an adamantinoma. Examples of the immature non-epithelial tumors include a simple sarcoma, a fibrosarcoma, a myxosarcoma, a liposarcoma, an osteosarcoma, a melanosarcoma, and a rhabdomyosarcoma.

In particular, a metastatic brain tumor (Brain metastasis) refers to a tumor made as a primary tumor is transferred to a brain along a blood vessel. When the brain metastasis may be fatal to life of a patient with the malignant tumor.

The metastatic brain tumors have various sizes and mostly have spherical shapes.

However, because the metastatic brain tumor is observed as having a brightness value similar to a brightness value of a white matter in a T1-weighted MRI image, there is a problem in that it is difficult to diagnose the metastatic brain tumor with a traditional image-based analysis technique.

Recently, a practitioner diagnoses the metastatic brain tumor by finding lesions while analyzing the images one by one.

There have been attempts to apply an automated method and studies for diagnosis with various types of images in addition to the T1-MRI images. However, these studies are conducted based on 2D images, there are severe problems in that there are interruptions between slices during reconfiguration processes, which deteriorates detection accuracy.

DOCUMENT OF RELATED ART

Patent Documents

1. Korean Patent No. 10-1793609 (published on Nov. 6, 2017)
2. Korean Patent No. 10-2072476 (published on Feb. 3, 2020)

SUMMARY

The present disclosure has been made in an effort to solve the above-mentioned problems, and an object of the present disclosure is to provide a user with a device and a method for detecting a tumor using a medical image and diagnosing a shape and a property of the detected tumor.

More particularly, the object of the present disclosure is to provide a user with a device and a method for detecting a tumor by adopting artificial intelligence (AI) based on medical imaging and patient information, diagnosing a shape and a property of the detected tumor, and providing information on prognosis prediction, thereby providing information suitable to allow a medical practitioner to diagnose a patient and establish a treatment plan.

The present disclosure is intended to implement automation of tumor detection by reducing difficulty in obtaining images by using only T1-MRI and using a 3D deep neural network that can use spatial information.

The present disclosure, to which a system for detecting and diagnosing a lesion in a 3D medical image is applied, may also be applied to lesions such as brain tumors, metastatic brain tumors, lung cancer, breast cancer, liver cancer, colorectal cancer, prostate cancer, cervical cancer, pancreatic cancer, and may also be applied to lung calcification and brain white matter hyperintensity.

In particular, an object of the present disclosure is to implement automation of detection of a brain tumor/metastatic tumor, and to provide a medical team with information on a risk degree and a treatment priority by predicting prognosis by converting the number of lesions, the size, and other information, as trackers for metastatic brain tumor (brain metastasis), into numerical values and combining the numerical values with information of the patient's age and state and the time of onset.

Furthermore, an object of the present disclosure is to assist a patient and a medical team in predicting a shape of a lesion and coping in advance with the lesion.

In addition, an object of the present disclosure is to obtain more professional medical findings and treatment by sharing data with a medical team, immediately after the generation of the diagnosis result, for an interaction with the medical team, and by proposing attending physicians or medical teams suitable for locations and properties of lesions or sending a request to the corresponding medical team.

In addition, an object of the present disclosure is to propose a treatment according to a history, provide a treatment (history) suitable for locations or properties of lesions by sharing the data with the medical team, and thus consistently perform feedback during use, thereby providing an appropriate proposal that becomes more suitable as the device is used for a long period of time.

Meanwhile, technical problems to be solved by the present disclosure are not limited to the above-mentioned technical problems, and other technical problems, which are not mentioned above, may be clearly understood from the following descriptions by those skilled in the art to which the present disclosure pertains.

In order to achieve the above-described technical objects, a medical image-based tumor detection and diagnostic device according to one aspect of the present disclosure includes: an input unit configured to obtain a medical image related to a patient; a preprocessing unit configured to preprocess the obtained medical image to improve analysis performance; an analysis unit configured to divide the preprocessed image into a plurality of regions by applying a deep neural network-based deep learning technique; and a measurement unit configured to group the plurality of divided regions by performing clustering on the plurality of divided regions, in which the measurement unit extracts a group feature value in respect to each of the grouped regions and derives diagnosis information related to the tumor based on the extracted group feature value.

In addition, the input unit may further obtain body information of the patient, and the measurement unit may derive the diagnosis information using both the group feature value and the body information.

In addition, the preprocessing unit may align a direction of the obtained medical image, correct signal deflection in the image to implement uniformity in the obtained medical image, and remove a region in the obtained medical image except for a body organ region which is a target.

In addition, the analysis unit may resample the preprocessed image based on voxel resolution to correct resolution, normalize the resampled image, adjusts a size of the normalized image to apply the deep neural network-based deep learning technique, and divide the image with the adjusted size into a plurality of regions to implement an output equal in magnitude to an input of the deep neural network.

In addition, an image inputted to the deep neural network and an image related to the plurality of divided regions may be three-dimensional images.

In addition, the deep neural network-based deep learning technique may use a DSC (depth-wise separable convolution) block capable of reducing the number of variables and the number of arithmetic operations by changing at least one of an arithmetic operation order and an arithmetic method.

In the application of the DSC block, the deep neural network-based deep learning technique may apply skip-connection to prevent a loss of information in the image inputted to the deep neural network.

In addition, the deep neural network-based deep learning technique may use an ASPP (Atrous spatial pyramid pooling) block for performing multi-scale pooling, over a plurality of steps, on an Atrous convolution for performing a wider FOV (field of view) arithmetic operation with the same number of parameters by expanding a convolution filter.

In addition, the deep neural network-based deep learning technique may use up-and-down sampling to obtain a plurality of features derived in accordance with a plurality of scales.

In addition, the measurement unit may perform the clustering to process the tumor from a voxel level to an object level.

In addition, the measurement unit may quantify the extracted group feature value, and the diagnosis information may include information on a location, a region, a diameter, and a volume of the tumor.

In addition, the measurement unit may predict prognosis related to the tumor by combining clinical information and the object level information.

In addition, the medical image-based tumor detection and diagnostic device may further include an output unit configured to output the grouped region and the group feature value.

In addition, the medical image-based tumor detection and diagnostic device may further include a storage unit configured to perform reverse processing on matrix information obtained by a grouping operation of the measurement unit so that the matrix information matches an original medical image space obtained by the input unit and then store the matrix information, in which the storage unit stores the grouped region and the group feature value.

In addition, the tumor may include brain cancer, metastatic brain cancer, lung cancer, breast cancer, liver cancer, colorectal cancer, prostate cancer, cervical cancer, and pancreatic cancer.

In addition, the preprocessing unit may preprocess the obtained medical image in order to observe at least one of a lung calcification region and a brain white matter hyperintensity region in addition to the tumor region.

As described above, according to the present disclosure, it is possible to provide a user with the device and the method for detecting a tumor using a medical image and diagnosing a shape and a property of the detected tumor.

Specifically, the present disclosure may provide a user with a device and a method for detecting a tumor by adopting artificial intelligence (AI) based on medical imaging and patient information, diagnosing a shape and a property of the detected tumor, and providing information on prognosis prediction, thereby providing information suitable to allow a medical practitioner to diagnose a patient and establish a treatment plan.

The present disclosure may implement automation of tumor detection by reducing difficulty in obtaining images by using only T1-MRI and using a 3D deep neural network that can use spatial information.

In addition, the present disclosure, to which the system for detecting and diagnosing a lesion in a 3D medical image is applied, may also be applied to lesions such as brain tumors, metastatic brain tumors, lung cancer, breast cancer, liver cancer, colorectal cancer, prostate cancer, cervical cancer, pancreatic cancer, and may also be applied to lung calcification and brain white matter hyperintensity.

In particular, the present disclosure may implement automation of detection of a brain tumor/metastatic tumor, and provide a medical team with information on a risk degree and a treatment priority by predicting prognosis by converting the number of lesions, the size, and other information, as trackers for metastatic brain tumor (brain metastasis), into numerical values and combining the numerical values with information of the patient's age and state and the time of onset.

Furthermore, the present disclosure may assist a patient and a medical team in predicting a shape of a lesion and coping in advance with the lesion.

In addition, the present disclosure may obtain more professional medical findings and treatment by sharing data with a medical team, immediately after the generation of the diagnosis result, for an interaction with the medical team, and by proposing attending physicians or medical teams suitable for locations and properties of lesions or sending a request to the corresponding medical team.

In addition, the present disclosure may propose a treatment according to a history, provide a treatment (history) suitable for locations or properties of lesions by sharing the data with the medical team, and thus consistently perform feedback during use, thereby providing an appropriate proposal that becomes more suitable as the device is used for a long period of time.

Meanwhile, the effects obtained by the present disclosure are not limited to the aforementioned effects, and other effects, which are not mentioned above, will be clearly understood by those skilled in the art from the following description.

BRIEF DESCRIPTION OF THE DRAWINGS

The above and other aspects, features and other advantages of the present disclosure will be more clearly understood from the following detailed description taken in conjunction with the accompanying drawings, in which.

DETAILED DESCRIPTION OF THE EMBODIMENT

Figure 1:
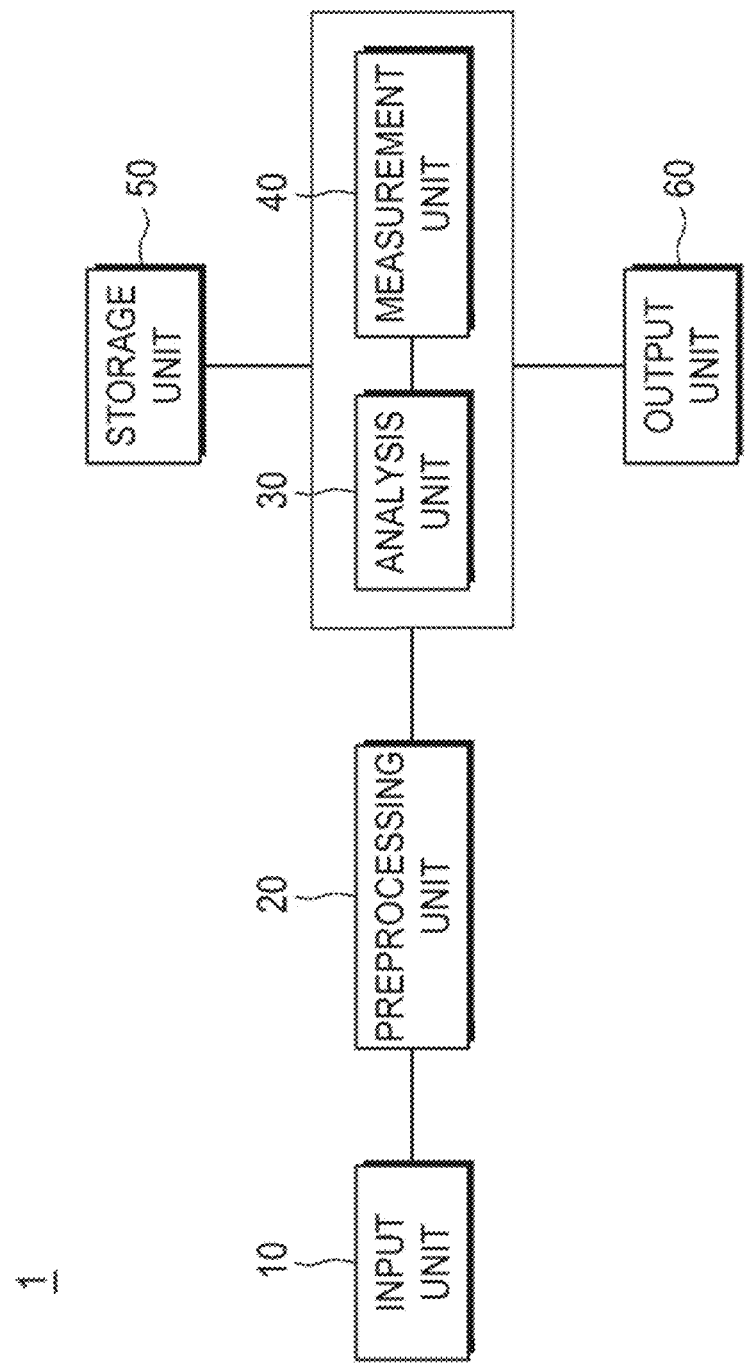
FIG. 1 is a block configuration view illustrating a tumor detection and diagnostic device according to the present disclosure.

Hereinafter, exemplary embodiments of the present disclosure will be described with reference to the drawings. In addition, the exemplary embodiment described below does not unfairly limit the contents of the present disclosure disclosed in the claims, and all of the constituent elements described in the exemplary embodiment are not essential as technical solutions of the present disclosure.

Hereinafter, a device and a method for detecting a tumor using a medical image and diagnosing a shape and a property of the detected tumor according to the exemplary embodiment of the present disclosure will be described in detail with reference to the accompanying drawings.

Metastatic Brain Tumor (Brain Metastasis)

The present disclosure may be used to detect various tumors and diagnose shapes and properties of the detected tumors.

For example, the tumor to which the present disclosure may be applied may include brain cancer, metastatic brain cancer, lung cancer, breast cancer, liver cancer, colorectal cancer, prostate cancer, cervical cancer, and pancreatic cancer.

In addition, the present disclosure may also be used to detect a lung calcification region and a brain white matter hyperintensity region in addition to the tumor region and diagnose properties of the corresponding regions.

Hereinafter, the present disclosure will be described, focusing on a metastatic brain tumor (brain metastasis) which is a representative tumor.

However, the scope of the present disclosure is not limited to the metastatic brain tumor, and the present disclosure may be used to detect and diagnose brain cancer, lung cancer, breast cancer, liver cancer, colorectal cancer, prostate cancer, cervical cancer, pancreatic cancer, a lung calcification region, a brain white matter hyperintensity region, and the like.

A metastatic brain tumor is caused as a primary tumor located outside a cranial cavity spread to the inside of the cranial cavity, and the metastatic brain tumor is the most common malignant tumor in the brain of the adult. The brain is a part to which systemic cancer such as lung cancer or breast cancer spreads comparatively commonly, and it is estimated that approximately about 20 to 30% of all the patients with systemic cancer suffer from the metastatic brain tumors (Gavrilovic I T, Posner J B. J Neurooncol. 2005; 751:5-14).

Even in Korea, there an increase in total number of patients with cancer and patients with new malignant tumors, and it is estimated that there will be a steady increase in occurrence frequency of the metastatic brain tumors.

In the case of the metastatic brain tumor, an overall survival (OS) period is short than otherwise.

In the case of lung cancer that accounts for 50% or more of the overall primary foci of the metastatic brain tumors, there is a research result indicating that a patient group for which brain MRI is performed as a pre-operation screening test, whether the presence of brain metastasis is checked, and an appropriate treatment is performed has a significantly higher survival rate than a patient group that is not subjected to the above-mentioned processes.

In addition, there is a report indicating that it is possible to increase a survival rate of patients with the metastatic brain tumor in accordance with complex and active treatments such as recent chemotherapy, radiation therapy and gamma knife surgeries.

Therefore, in order to improve prognosis of the patient, it is very important to find early the presence or absence of brain metastasis in the cancer patient.

The basic test for diagnosing the metastatic brain tumor is brain MRI. Because the MRI is excellent in illumination intensity from soft tissue in comparison with the computerized tomography (CT), has less artifacts caused by the cranium, and has a number of advantages of high contrast enhancement, the MRI is a very important divide for diagnosing the metastatic brain tumor.

In the case of MRI, because the contrast enhancement allows normal blood vessels as well as the metastatic tumor node to be observed, it is necessary to appropriately distinguish the small brain metastasis node from the normal blood vessel.

To this end, it is necessary to carefully determine whether a lesion, which is shown by the contrast enhancement, has a spherical shape or an irregular shape or whether the lesion has a cylindrical shape like the blood vessel. However, in some instances, it is not easy to distinguish the node and the blood vessel even though a high-resolution image is used.

In addition, in the case of high-resolution MRI, the number of image slices obtained for each test is significantly large. For this reason, the process of accurately analyzing the image slices one by one is a great burden to radiologists who read out the images.

All the imaging tests inherently have a risk of occurrence of readout errors. In particular, while more accurate imaging diagnosis is required as medical technologies are improved, the number of imaging tests explosively increases, and the time it takes to read out the high-resolution images becomes longer. As a result, the burden to the radiologists also greatly increases. Therefore, there is a need for a safety device capable of reducing a risk of readout errors.

Accordingly, in order to solve the above-mentioned problem, the present disclosure is intended to provide a device and a method for automatically detecting, dividing, analyzing, and diagnosing brain metastasis nodes in medical images of brains by using image processing and artificial intelligence technologies.

Medical Image-Based Tumor Detection and Diagnostic Device

The present disclosure has been made in an effort to solve the above-mentioned problems, and an object of the present disclosure is to provide a user with a device and a method for detecting a tumor using a medical image and diagnosing a shape and a property of the detected tumor.

More particularly, the object of the present disclosure is to provide a user with a device and a method for detecting a tumor by adopting artificial intelligence (AI) based on medical imaging and patient information, diagnosing a shape and a property of the detected tumor, and providing information on prognosis prediction, thereby providing information suitable to allow a medical practitioner to diagnose a patient and establish a treatment plan.

The present disclosure is intended to implement automation of tumor detection by reducing difficulty in obtaining images by using only T1-MRI and using a 3D deep neural network that can use spatial information.

The present disclosure, to which a system for detecting and diagnosing a lesion in a 3D medical image is applied, may also be applied to lesions such as brain tumors, metastatic brain tumors, lung cancer, breast cancer, liver cancer, colorectal cancer, prostate cancer, cervical cancer, pancreatic cancer, and may also be applied to lung calcification and brain white matter hyperintensity.

In particular, an object of the present disclosure is to implement automation of detection of a brain tumor/metastatic tumor, and to provide a medical team with information on a risk degree and a treatment priority by predicting prognosis by converting the number of lesions, the size, and other information, as trackers for metastatic brain tumor (brain metastasis), into numerical values and combining the numerical values with information of the patient's age and state and the time of onset.

Furthermore, an object of the present disclosure is to assist a patient and a medical team in predicting a shape of a lesion and coping in advance with the lesion.

In addition, an object of the present disclosure is to obtain more professional medical findings and treatment by sharing data with a medical team, immediately after the generation of the diagnosis result, for an interaction with the medical team, and by proposing attending physicians or medical teams suitable for locations and properties of lesions or sending a request to the corresponding medical team.

In addition, an object of the present disclosure is to propose a treatment according to a history, provide a treatment (history) suitable for locations or properties of lesions by sharing the data with the medical team, and thus consistently perform feedback during use, thereby providing an appropriate proposal that becomes more suitable as the device is used for a long period of time.

FIG. 1 is a block configuration view illustrating a tumor detection and diagnostic device according to the present disclosure.

As illustrated in FIG. 1, a tumor detection and diagnostic device 1 according to an exemplary embodiment of the present disclosure may include an input unit 10, a preprocessing unit 20, an analysis unit 30, a measurement unit 40, a storage unit 50, and an output unit 60.

First, the input unit 10 may obtain a medical image related to a patient.

Specifically, the input unit 10 may obtain Head & Neck single MRI medical images having DICOM or NIFTI information.

In addition, the input unit 10 may obtain body information related to the patient, and the body information may include gender, age, information acquisition time, and the like.

Next, the preprocessing unit 20 serves to preprocess the obtained medical image to observe a tumor region.

Representatively, the preprocessing unit 20 may provide a function of aligning a direction of the image, a function of correcting signal deflection in the image (correcting non-uniformity in the image), and a function of removing regions other than a brain region (extracting the brain region).

In addition, the analysis unit 30 provides a function of dividing the preprocessed image into a plurality of regions by applying a deep neural network-based deep learning technique.

Representatively, the analysis unit 30 may provide image resampling, image normalization, image-size adjustment, and a deep learning-based image division function.

In addition, the measurement unit 40 provides a function of grouping the plurality of divided regions by performing clustering on the plurality of divided regions.

In addition, the measurement unit 40 extracts a group feature value in respect to each of the grouped regions and derives diagnosis information related to the tumor based on the extracted group feature value.

Representatively, the measurement unit 40 may provide a function of grouping the divided regions, a function of measuring and quantifying the respective group feature values, a function of calculating prognosis prediction information.

In addition, the output unit may output the grouped region and the group feature value.

In addition, the storage unit 50 may perform reverse processing on matrix information obtained by a grouping operation of the measurement unit 40 so that the matrix information matches an original medical image space obtained by the input unit 10 and then store the matrix information.

In addition, the storage unit 50 may also store the grouped region and the group feature value.

Lastly, the output unit 60 provides a function of outputting the grouped region and the group feature value.

Figure 2:
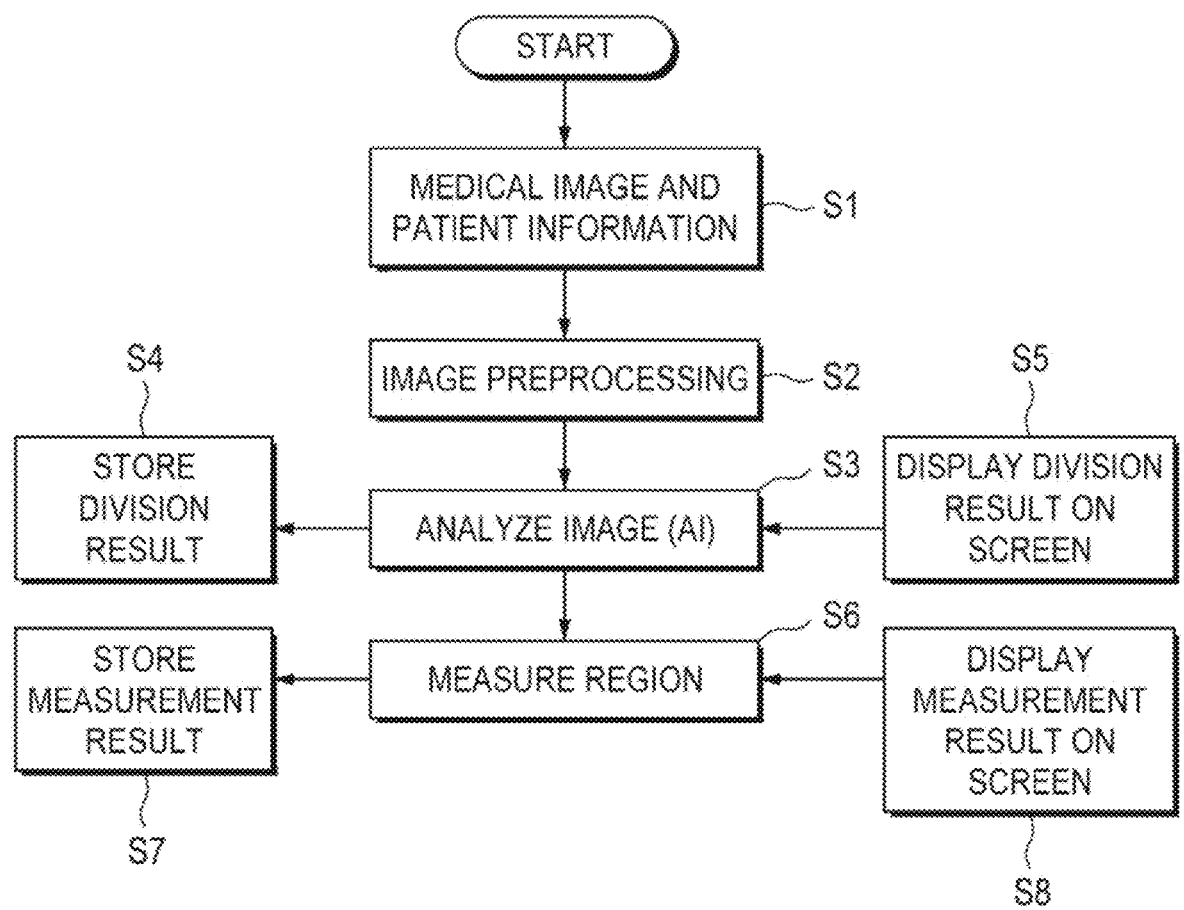
FIG. 2 is a flowchart for explaining a medical image-based tumor detection and diagnosis method according to the present disclosure.

FIG. 2 is a flowchart for explaining a medical image-based tumor detection and diagnosis method according to the present disclosure.

Referring to FIG. 2, an input unit 10 performs a step S1 of obtaining a medical image related to a patient.

In this case, the input unit 10 may additionally obtain body information of the patient, and then the measurement unit 40 may derive the diagnosis information using both the group feature value and the body information.

In addition, the preprocessing unit 20 performs a step S2 of preprocessing the obtained medical image to observe a tumor region.

In this case, the preprocessing unit 20 may align a direction of the obtained medical image, correct signal deflection in the image to implement uniformity in the obtained medical image and remove a region in the obtained medical image except for the tumor region which is a target.

Thereafter, the analysis unit 30 performs a step S3 of dividing the preprocessed image into a plurality of regions by applying a deep neural network-based deep learning technique.

In this case, the analysis unit 30 may resample the preprocessed image based on voxel resolution to correct resolution, normalize the resampled image, adjusts a size of the normalized image to apply the deep neural network-based deep learning technique, and divide the image with the adjusted size into a plurality of regions to implement an output equal in magnitude to an input of the deep neural network.

In addition, the image inputted to the deep neural network and the image related to the plurality of divided regions may be three-dimensional images.

In this case, the storage unit 50 may store a division result (S4), and the output unit 60 may display the division result (S5).

In addition, the measurement unit 40 may group the plurality of divided regions by performing clustering on the plurality of divided regions, extract the group feature value in respect to each of the grouped regions, and derive the diagnosis information related to the tumor based on the extracted group feature value (S6).

In this case, the measurement unit 40 may perform the clustering to process the tumor from a voxel level to an object level.

In addition, the measurement unit 40 may quantify the extracted group feature value, and the diagnosis information may include information on a location, a region, a diameter, and a volume of the tumor.

In addition, the measurement unit 40 may also predict prognosis related to the tumor by combining clinical information and the object level information.

Thereafter, the storage unit 50 may perform a step S7 of storing the grouped region and the group feature value.

In this case, the storage unit 50 may perform reverse processing on the matrix information obtained by the grouping operation of the measurement unit so that the matrix information matches the original medical image space obtained by the input unit and then store the matrix information.

In addition, the output unit 60 may output the grouped region and the group feature value.

As described above, the tumor may include brain cancer, metastatic brain cancer, lung cancer, breast cancer, liver cancer, colorectal cancer, prostate cancer, cervical cancer, and pancreatic cancer.

In addition, the preprocessing unit 20 may preprocess the obtained medical image in order to observe at least one of a lung calcification region and a brain white matter hyperintensity region in addition to the tumor region.

Hereinafter, the roles and functions of the components will be specifically described with reference to the drawings.

Configuration and Operation of Input Unit

Figure 3:
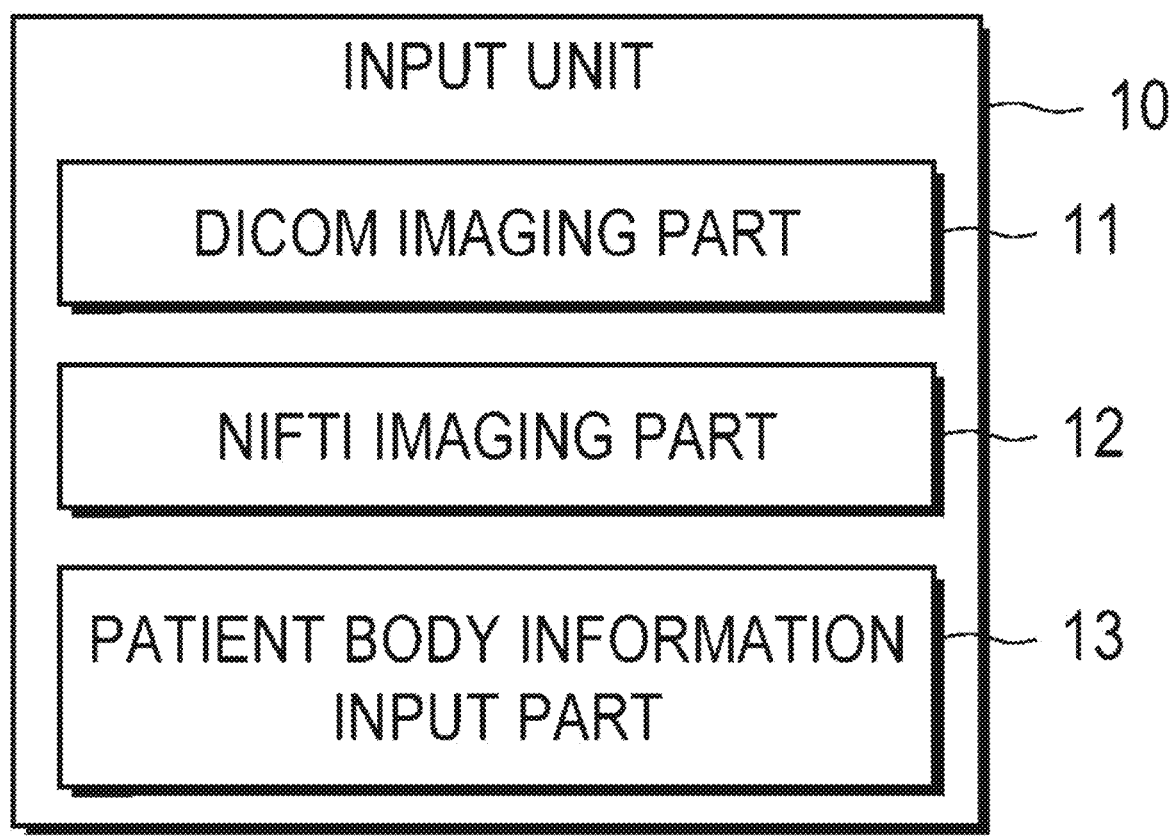
FIG. 3 is a block configuration view illustrating an input unit applied to the tumor detection and diagnostic device according to the present disclosure.

FIG. 3 is a block configuration view illustrating the input unit applied to the tumor detection and diagnostic device according to the present disclosure.

The input unit 10 according to the present disclosure may obtain the medical image related to the patient.

In this case, the input unit 10 may include a DICOM imaging part 11 configured to obtain DICOM information corresponding to Head & Neck single MRI images, and an NIFTI imaging part 12 configured to obtain NIFTI information.

In addition, the input unit 10 may further include a patient body information input part 13 configured to additionally obtain the body information. In this case, the body information may include basic patient information such as gender and age, information acquisition time, and the like.

Configuration and Operation of Preprocessing Unit

Figure 4:
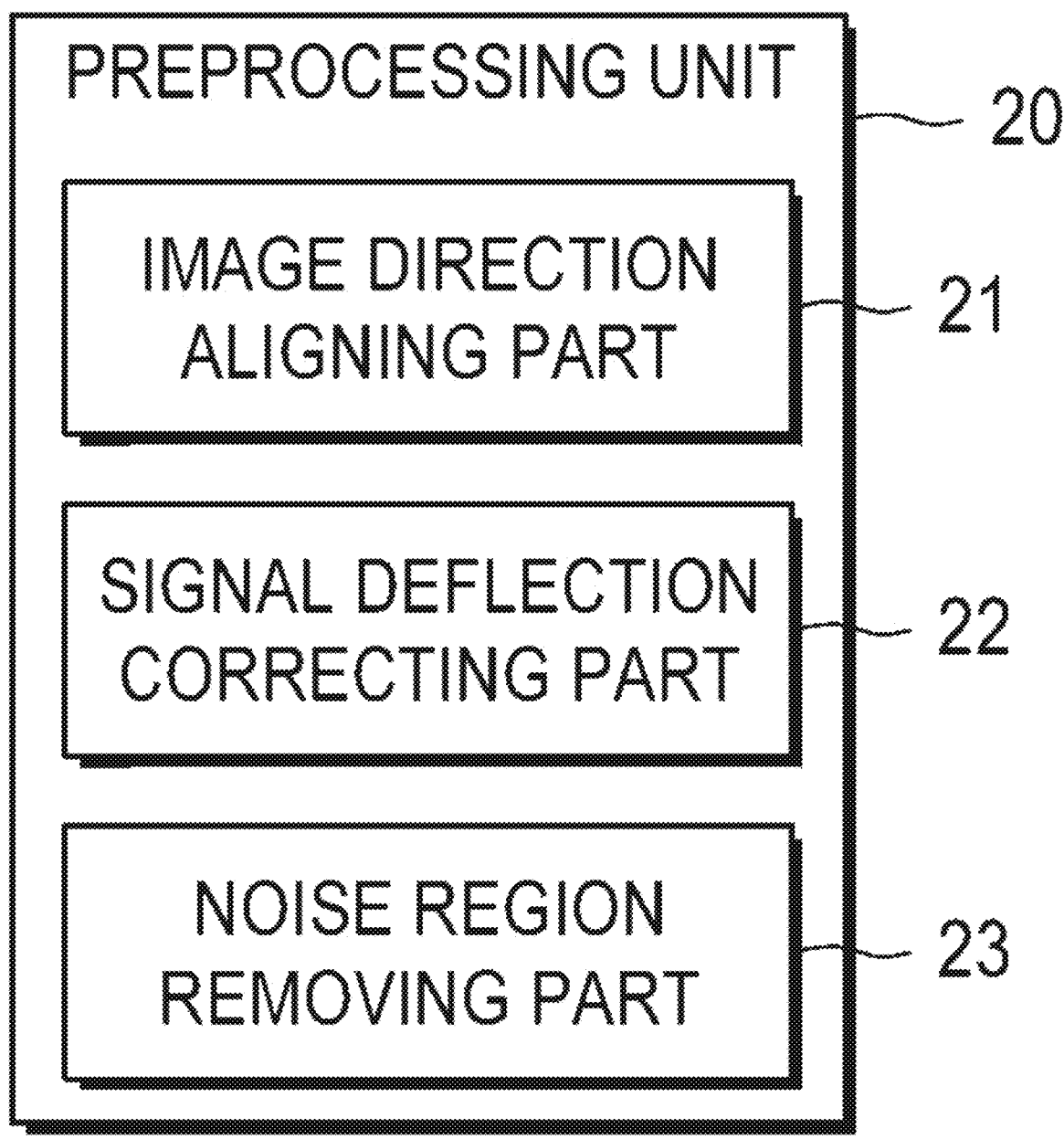
FIG. 4 is a block configuration views illustrating a preprocessing unit applied to the tumor detection and diagnostic device according to the present disclosure.

FIG. 4 is a block configuration view illustrating the preprocessing unit applied to the tumor detection and diagnostic device according to the present disclosure.

Referring to FIG. 4, the preprocessing unit 20 may include an image direction aligning part 21 using RPI orientation alignment, an in-image signal deflection correcting part 22 configured to correct non-uniformity in the image, and a region removing part 23 configured to remove a region other than a brain region to extract the brain region in which the tumor is present.

In this case, the signal deflection correcting part 22 may apply non-uniformity correction or the like, and the noise region removing part 23 may apply skull-stripping or the like.

Figure 5B:
FIGS. 5A and 5B are views illustrating an example of an operation of the preprocessing unit according to the present disclosure.
Figure 5A:

Meanwhile, FIGS. 5A and 5B are views illustrating an example of an operation of the preprocessing unit according to the present disclosure.

FIG. 5A illustrates DICOM medical information obtained by the input unit 10, and FIG. 5B illustrates a result of aligning the image direction, correcting the signal deflection in the image, and extracting the brain region by the preprocessing unit 20.

In addition, the preprocessing unit 20 may preprocess the obtained medical image in order to observe at least one of a lung calcification region and a brain white matter hyperintensity region in addition to the tumor region.

Configuration and Operation of Analysis Unit

Figure 6:
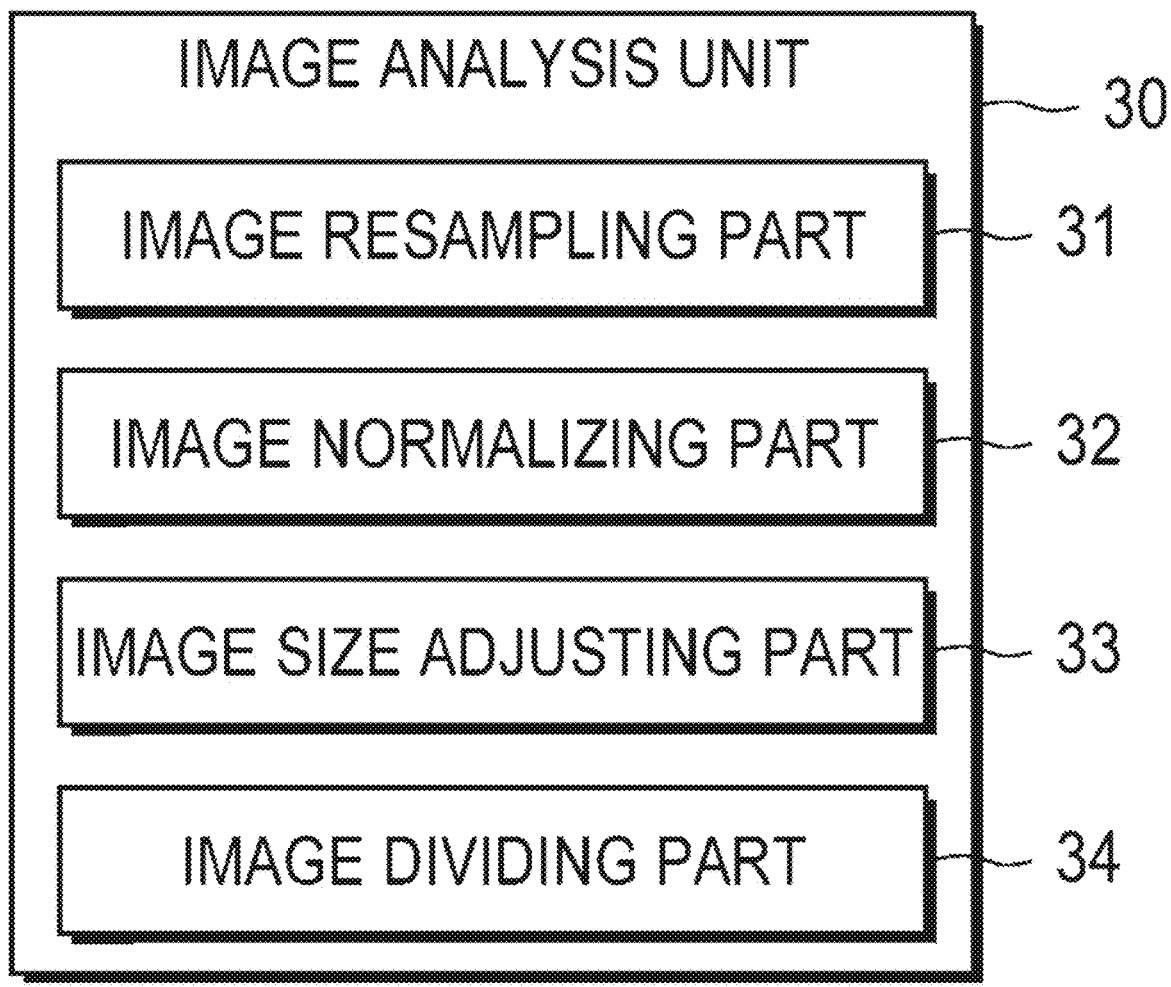
FIG. 6 is a block configuration view illustrating an image analysis unit applied to the tumor detection and diagnostic device according to the present disclosure.

FIG. 6 is a block configuration view illustrating the image analysis unit applied to the tumor detection and diagnostic device according to the present disclosure, and FIGS. 7A and 7B are view illustrating an example of an operation of the image analysis unit according to the present disclosure.

Referring to FIG. 6, the analysis unit 30 performs the step S3 of dividing the preprocessed image into the plurality of regions by applying the deep neural network-based deep learning technique.

In this case, the analysis unit 30 may include an image resampling part 31 configured to resample the preprocessed image based on voxel resolution to correct resolution, an image normalizing part 32 configured to normalize the resampled image, an image size adjusting part 33 configured to adjusts a size of the normalized image to apply the deep neural network-based deep learning technique, and an image dividing part 34 configured to divide the image with the adjusted size into a plurality of regions to implement an output equal in magnitude to an input of the deep neural network.

In this case, the image inputted to the deep neural network and the image related to the plurality of divided regions may be three-dimensional images.

Figure 7:
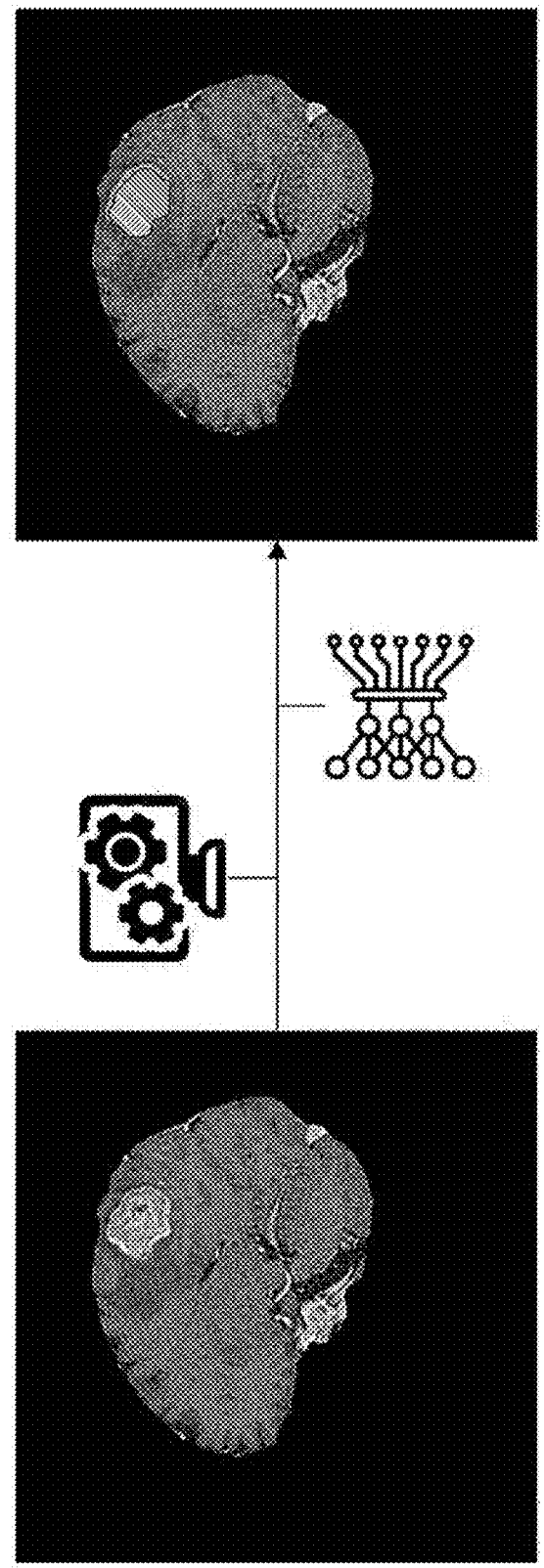
FIG. 7 is a view illustrating an example of an operation of the image analysis unit according to the present disclosure.

FIG. 7 is a views illustrating an example of an image preprocessed by the preprocessing unit 20 before being subjected to the analysis unit 30 (left image), and an image as a result of dividing the image into the plurality of regions by the analysis unit 30 (right image).

Specifically, the image resampling part 31 performs resampling based on voxel-resolution in order to correct resolution that varies depending on the images, and an image of 0.5 mm×0.5 mm×0.5 mm may be applied.

However, the image of 0.5 mm×0.5 mm×0.5 mm is just a simple example to be applied to the present disclosure, and it is apparent that multiple types of voxel resolution having different conditions may be applied.

In addition, as a representative example, the image normalizing part 32 performs normalization with (m, σ)=(0, 1) and applies an intensity clip with a maximum value 6.

Likewise, the application of the maximum value of 6 is an example to be applied to the present disclosure, and other maximum values may be applied.

In addition, the image size adjusting part 33 adjusts a size of the image corresponding to a deep neural network analysis to be performed later, and a size of an array may be 176×176×176.

In addition, the image dividing part 34 performs a deep neural network-based target region segmentation and implements an output equal in magnitude to an input of the deep neural network, and representatively, a size of 176×176×176 may be applied.

Likewise, the application of the size of 176×176×176 is an example to be applied to the present disclosure, and other sizes may be applied.

In this case, a DSC (depth-wise separable convolution) block, skip-connection, an ASPP (Atrous spatial pyramid pooling) block, up-and-down sampling, and the like may be used.

The depth-wise separable convolution means a separable convolution for each depth, and the Atrous spatial pyramid pooling means hole space pyramid pooling.

Figure 8:
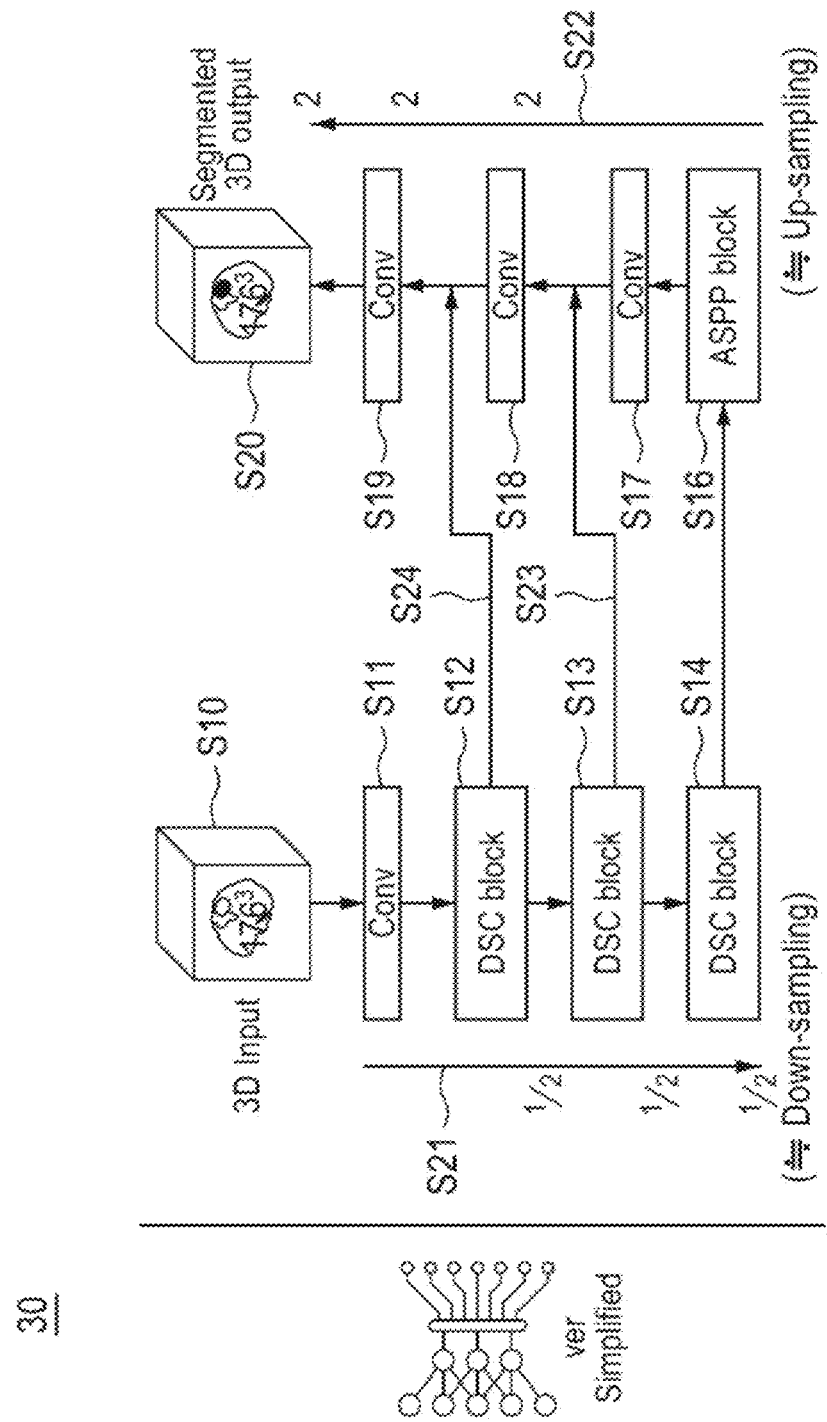
FIG. 8 is a flowchart illustrating an operation of the image analysis unit according to the present disclosure.

FIG. 8 is a flowchart illustrating a specific operation of the image dividing part 34.

First, referring to FIG. 8, the image inputted to the deep neural network and the image related to the plurality of divided regions may be three-dimensional images.

In a case in which a 2D model is applied and reproduced to a 3D image by combining the resultant slices, there is a problem in that disconnection occurs between the slices and it is difficult to consider a global location.

Therefore, in the present disclosure, a 3D model is applied, such that the disconnection between the slices may be removed and the whole location may be considered.

Because the metastatic brain tumor (brain metastasis) often has a spherical shape instead of a circular shape, there is an advantage in that the 3D model makes it possible to reasonably determine the metastatic brain tumor.

Referring to FIG. 8, a three-dimensional image is inputted to the deep neural network (S10), a primary convolution is performed (S11), and an arithmetic operation with the applied DSC (depth-wise separable convolution) block is performed three times (S12, S13, and S14).

In this case, skip-connection may be performed between the arithmetic operations with the DSC (depth-wise separable convolution) block (S23 and S24).

After the step S14, an arithmetic operation with the applied ASPP (Atrous spatial pyramid pooling) block is performed, the convolution is performed three times (S17, S18, and S19), and then the three-dimensional image related to the plurality of divided regions is outputted (S20).

In this case, with a combination of a result of performing the skip-connection twice (S23 and S24) and a result of performing the convolution twice (S17 and S18) is used as an input value in the next convolution (S18 and S19).

In particular, the final convolution (S19) is used to obtain a final probability value, as follows.

0=Normal/Background
1=BM

In this case, the DSC (depth-wise separable convolution) block is used to reduce the number of variables and the number of arithmetic operations by changing at least one of an arithmetic operation order and an arithmetic method.

The DSC is a conv module that greatly reduces the number of variables and the number of arithmetic operations by changing the arithmetic operation order and the arithmetic method of general conv while maintaining the arithmetic operation information in a similar way to the related art. When the DSC, which is performed over several steps, is applied into the model, it is possible to efficiently cope with various FOV, and as a result, it is possible to more appropriately detect an object having various sizes like the metastatic brain tumor.

In particular, when the DSC is used for a 3D model requiring a large quantity of resources, it is possible to effectively make the model lightweight, such that it is possible to detect BM having various sizes without disconnection between the slices.

In the application of the DSC block, the deep neural network-based deep learning technique may apply the skip-connection to prevent a loss of information in the image inputted to the deep neural network.

When the skip-connection is applied, a large number of sub-elements may be maintained, and as a result, it is possible to allow the model to more effectively perform the segmentation (division) operation.

In addition, the ASPP (Atrous spatial pyramid pooling) block for performing multi-scale pooling, over a plurality of steps, on the Atrous convolution for performing a wider FOV (field of view) arithmetic operation with the same number of parameters by expanding a convolution filter is used.

The ASPP block may advantageously obtain the output in consideration of even global characteristics as well as local characteristics. The ASPP block may be advantageous in detecting brain metastases having similar shapes but having various sizes.

In addition, up-and-down sampling to obtain a plurality of features derived in accordance with a plurality of scales may be used.

Configuration and Operation of Measurement Unit

Figure 9:
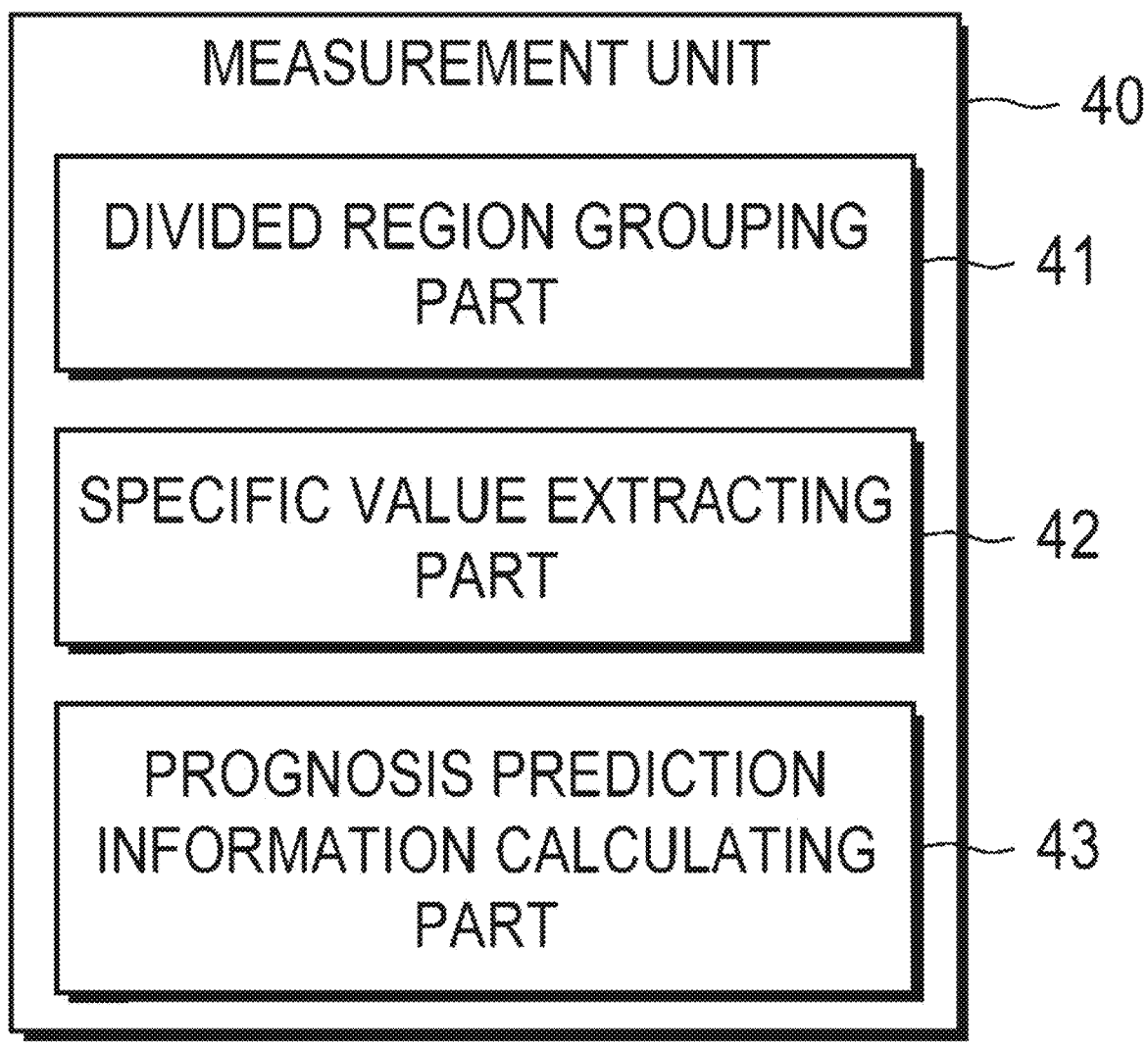
FIG. 9 is a block configuration view illustrating a measurement unit applied to the tumor detection and diagnostic device according to the present disclosure.
Figure 10C:
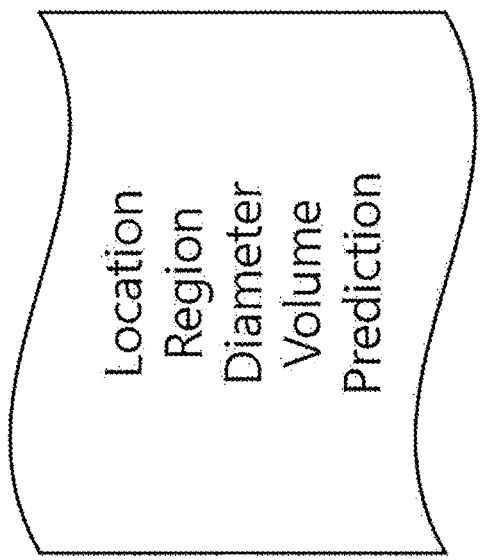
FIGS. 10A-10C are views illustrating an example of an operation of the measurement unit according to the present disclosure.
Figure 10B:
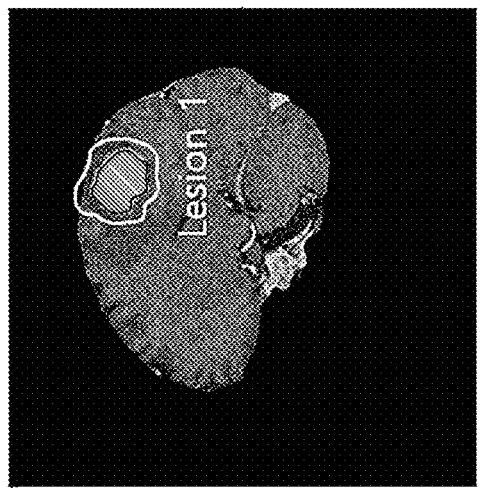
Figure 10A:
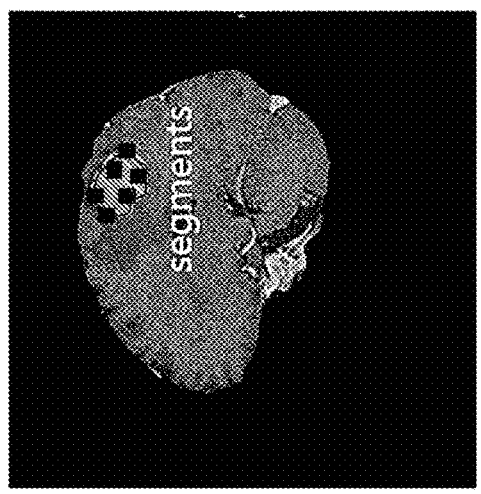

FIG. 9 is a block configuration view illustrating the measurement unit applied to the tumor detection and diagnostic device according to the present disclosure, and FIGS. 10A-10C are views illustrating an example of an operation of the measurement unit according to the present disclosure.

Referring to FIG. 9, the measurement unit 40 may include a grouping part 41 configured to group the plurality of divided regions by performing the clustering on the plurality of divided regions, an extracting part 42 configured to extract the group feature value in respect to each of the grouped regions, and a prognosis prediction information calculating part 43 configured to derive the diagnosis information related to the tumor based on the extracted group feature value.

The grouping part 41 may perform the clustering to process the tumor from the voxel level to the object level.

The extracting part 42 may quantify the extracted group feature value, and the diagnosis information may include information on a location, a region, a diameter, and a volume of the tumor.

The prognosis prediction information calculating part may also predict prognosis related to the tumor by combining clinical information and the object level information.

A progressing rate of a primary tumor, a location of a lesion in the brain, and the like may be related to the prognosis.

FIG. 10A is a view illustrating an example of an image divided into the plurality of regions passing through the analysis unit 30 before being subjected to the measurement unit 40, FIG. 10B is a view illustrating an example in which the plurality of divided regions is grouped by performing the clustering by the measurement unit 40, and FIG. 10C is a view illustrating an example in which the group feature value related to each of the grouped regions is extracted, and the diagnosis information related to the tumor is derived based on the extracted group feature value.

Meanwhile, the analysis unit 30 and the measurement unit 40 may apply MRI DICOM data open and MPR (multi planar reconstruction) implementation technologies.

That is, header and image information of MRI DICOM series may be read out by using ITK, a 3D volume may be reconfigured, reconfigured 3D Volume data may be potted by VTK, the 3D Volume may be converted by VTK library into MPR including a 2D image with an axial, coronal, and sagittal plane, and the MPR may be visualized on a screen.

In addition, the analysis unit 30 and the measurement unit 40 may apply a technology for detecting a candidate group of brain metastatic nodes.

Specifically, the candidate group of brain metastatic nodes may be detected by means of three-dimensional template matching and K-means clustering algorithm.

Because the brain metastatic node generally has a spherical shape, the brain metastatic node having a spherical shape may be detected by a spherical template having various size. The candidate groups of nodes having large sizes may be detected by means of K-means clustering based on the shape and pixel value in respect to the divided regions.

In addition, the analysis unit 30 and the measurement unit 40 may apply a machine learning (ANN) based candidate group determination model.

Specifically, based on the detected candidate groups of nodes, 272 characteristic values are extracted depending on histograms, shapes, and textures, and 30 characteristic values may be selected by means of the statistical technique.

In addition, the model based on the artificial neural network (ANN), among the machine learning techniques, may be learned by means of the selected 30 characteristic values.

Thereafter, the brain metastatic nodes may be finally detected by determining whether the node is present, targeting the node candidate groups previously detected by the learned ANN model.

In addition, the analysis unit 30 and the measurement unit 40 may perform the tumor detection using the deep learning model.

Specifically, there may be applied a cooperation of FC application S/W, a method of setting an environment for using the deep learning model in the Windows environment, a cooperative method of using the deep learning model, which is learned in the python environment, in application S/W executable in the Windows environment, a method of extracting the deep learning model in application S/W, a cooperative method of processing a deep learning result in application S/W, a CNN model for detecting a locations of nodes based on the nodes annotated by 3D VOI in an MRI image and dividing an outer periphery of the node, and settings for hyperparameters of the learned deep learning model and programs requiring a learning/executing environment.

Configurations and Operations of Storage Unit and Output Unit

Figure 11:
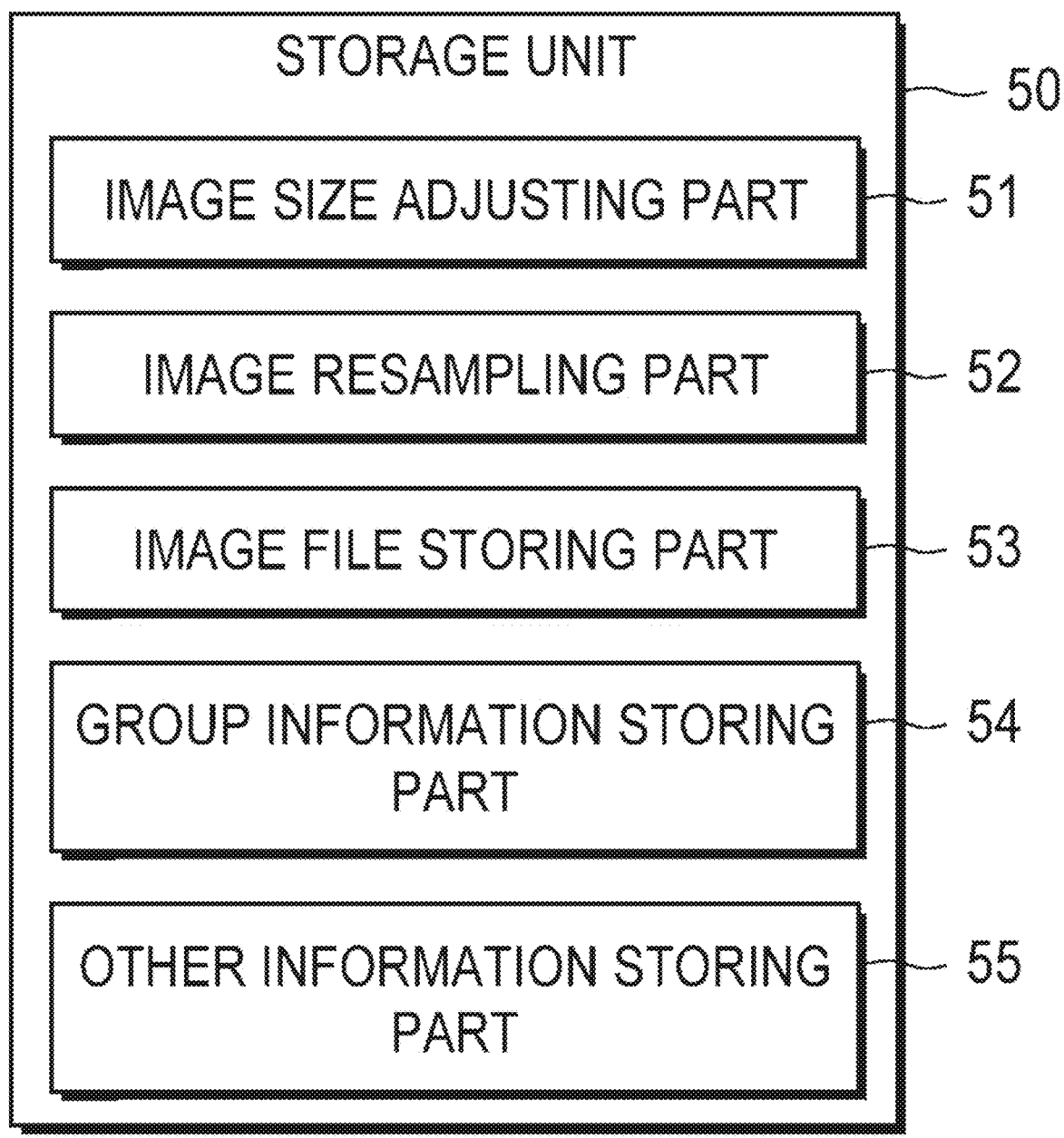
FIG. 11 is a block configuration view illustrating a storage unit applied to the tumor detection and diagnostic device according to the present disclosure.

FIG. 11 is a block configuration view illustrating the storage unit applied to the tumor detection and diagnostic device according to the present disclosure.

Referring to FIG. 11, the storage unit 50 may store the grouped region and the group feature value.

Specifically, the storage unit 50 may include an image size adjusting part 51, an image resampling part 52, an image file storing part 53, a group information storing part 54, another information storing part 55, and the like.

The storage unit 50 may perform reverse processing on the matrix information obtained by the grouping operation of the measurement unit so that the matrix information matches the original medical image space obtained by the input unit and then store the matrix information.

Figure 12:
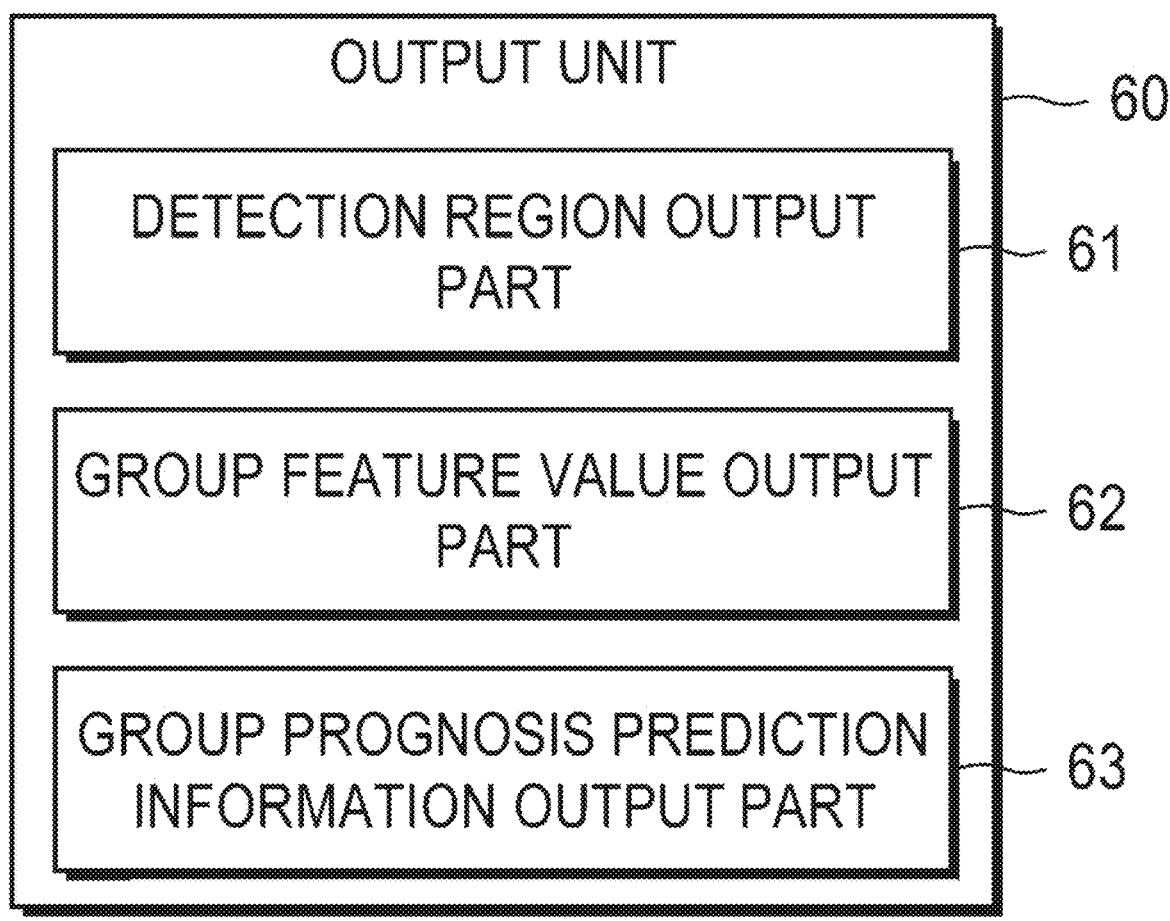
FIG. 12 is a block configuration view illustrating an output unit applied to the tumor detection and diagnostic device according to the present disclosure.

In addition, FIG. 12 is a block configuration view illustrating an output unit applied to the tumor detection and diagnostic device according to the present disclosure.

Referring to FIG. 12, the output unit 60 may output the grouped region and the group feature value.

Specifically, the output unit 60 may include a detection region output unit 61, a group feature value output part 62, and a group prognosis prediction information output part 63.

Figures 13A, 13B:
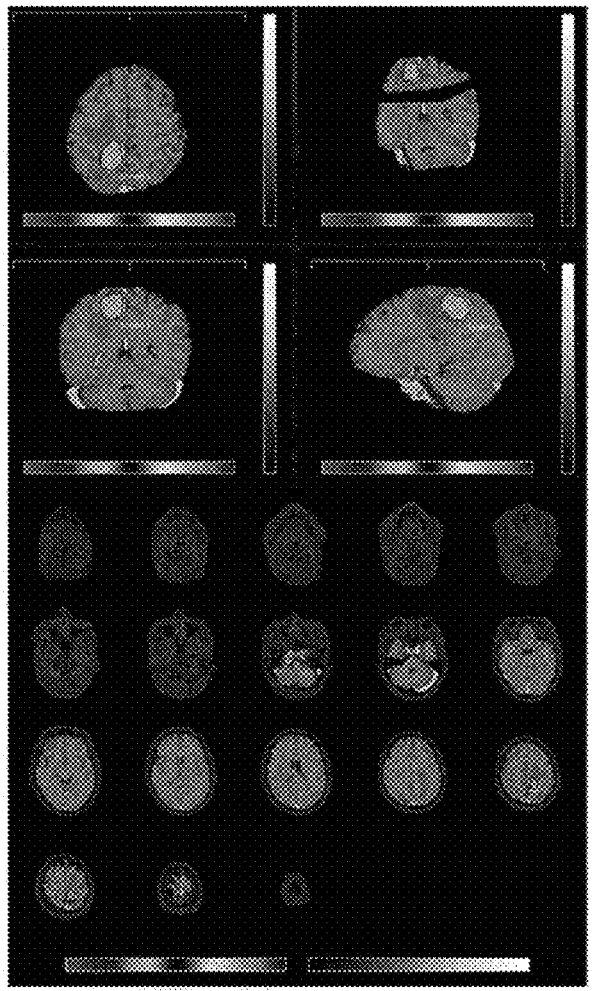
FIGS. 13A and 13B views illustrating an example of an operation of the output unit according to the present disclosure.

FIGS. 13A and 13B are views illustrating an example of an operation of the output unit according to the present disclosure.

FIG. 13A is a view illustrating an example of visualization of the detected region, and FIG. 13B is a view illustrating an example of a region group feature value and a prognosis prediction information output for each region group.

As described above, the tumor may include brain cancer, metastatic brain cancer, lung cancer, breast cancer, liver cancer, colorectal cancer, prostate cancer, cervical cancer, and pancreatic cancer.

In addition, the present disclosure may also detect and diagnose a lung calcification region and a brain white matter hyperintensity region in addition to the tumor region.

Advantageous Effects According to the Present Disclosure

According to the present disclosure, it is possible to provide a user with the device and the method for detecting a tumor using a medical image and diagnosing a shape and a property of the detected tumor.

Specifically, the present disclosure may provide a user with a device and a method for detecting a tumor by adopting artificial intelligence (AI) based on medical imaging and patient information, diagnosing a shape and a property of the detected tumor, and providing information on prognosis prediction, thereby providing information suitable to allow a medical practitioner to diagnose a patient and establish a treatment plan.

The present disclosure may implement automation of tumor detection by reducing difficulty in obtaining images by using only T1-MRI and using a 3D deep neural network that can use spatial information.

In addition, the present disclosure, to which the system for detecting and diagnosing a lesion in a 3D medical image is applied, may also be applied to lesions such as brain tumors, metastatic brain tumors, lung cancer, breast cancer, liver cancer, colorectal cancer, prostate cancer, cervical cancer, pancreatic cancer, and may also be applied to lung calcification and brain white matter hyperintensity.

In particular, the present disclosure may implement automation of detection of a brain tumor/metastatic tumor, and provide a medical team with information on a risk degree and a treatment priority by predicting prognosis by converting the number of lesions, the size, and other information, as trackers for metastatic brain tumor (brain metastasis), into numerical values and combining the numerical values with information of the patient's age and state and the time of onset.

Furthermore, the present disclosure may assist a patient and a medical team in predicting a shape of a lesion and coping in advance with the lesion.

In addition, the present disclosure may obtain more professional medical findings and treatment by sharing data with a medical team, immediately after the generation of the diagnosis result, for an interaction with the medical team, and by proposing attending physicians or medical teams suitable for locations and properties of lesions or sending a request to the corresponding medical team.

In addition, the present disclosure may propose a treatment according to a history, provide a treatment (history) suitable for locations or properties of lesions by sharing the data with the medical team, and thus consistently perform feedback during use, thereby providing an appropriate proposal that becomes more suitable as the device is used for a long period of time.

Meanwhile, the effects obtained by the present disclosure are not limited to the aforementioned effects, and other effects, which are not mentioned above, will be clearly understood by those skilled in the art from the following description.

The above-mentioned embodiments of the present disclosure may be implemented by various means. For example, the embodiments of the present disclosure may be implemented by hardware, firmware, software, or a combination thereof.

In the case of the implementation by hardware, the methods according to the embodiments of the present disclosure may be implemented by one or more of application specific integrated circuits (ASICs), digital signal processors (DSPs), digital signal processing devices (DSPDs), programmable logic devices (PLDs), field programmable gate arrays (FPGAs), processors, controllers, micro-controllers, micro-processor, and the like.

In the case of the implementation by firmware or software, the methods according to the embodiments of the present disclosure may be implemented in the form of modules, procedures, or functions for performing the above-mentioned functions or operations. A software code may be stored in a memory unit and executed by a processor. The memory unit is positioned inside and outside the processor and may transmit and receive data to/from the processor by means of various means already well known.

The detailed description of the exemplary embodiments of the present disclosure as described above has been provided to enable those skilled in the art to implement and carry out the present disclosure. While the present disclosure has been described above with reference to the exemplary embodiments, it may be understood by those skilled in the art that the present disclosure may be variously modified and changed without departing from the scope of the present disclosure. For example, those skilled in the art may use the components disclosed in the above-mentioned embodiments by combining the components. Therefore, the present disclosure is not limited to the embodiments disclosed herein but intended to provide the widest scope consistent with the principles and novel features disclosed herein.

The present disclosure may be specified as other specific forms without departing from the spirit and the essential features of the present disclosure. Therefore, it should be appreciated that the detailed description is interpreted as being illustrative in every sense, not restrictive. The scope of the present disclosure should be determined based on the reasonable interpretation of the appended claims, and all of the modifications within the equivalent scope of the present disclosure belong to the scope of the present disclosure. The present disclosure is not limited to the embodiments disclosed herein but intended to provide the widest scope consistent with the principles and novel features disclosed herein. In addition, the embodiments may be configured or new claims may be added by amendments after filing the application by combining claims that do not have explicit relationships therebetween.

What is claimed is:

1. A medical image-based tumor detection and diagnostic device comprising:
   an input unit configured to obtain a medical image related to a patient;
   a preprocessing unit configured to preprocess an obtained medical image to observe a tumor region;

an analysis unit configured to divide a preprocessed image into a plurality of regions by applying a deep neural network-based deep learning technique; and
a measurement unit configured to group a plurality of divided regions by performing a clustering on the plurality of divided regions, and further comprising:
an output unit configured to output one or more grouped region and a group feature value,
wherein:
the measurement unit extracts the group feature value in respect to each of the grouped regions and derives diagnosis information related to a tumor based on an extracted group feature value;
the analysis unit resamples the preprocessed image based on voxel resolution to correct resolution, normalizes a resampled image, adjusts a size of a normalized image to apply the deep neural network-based deep learning technique, and divides an image with an adjusted size into a plurality of regions to implement an output equal in magnitude to an input of the deep neural network,
wherein an image inputted to the deep neural network and an image related to the plurality of divided regions are three-dimensional images;
the measurement unit performs the clustering to process the tumor from a voxel level to an object level;
the measurement unit quantifies the extracted group feature value, and the diagnosis information includes information on a location, a region, a diameter, and a volume of the tumor;
the input unit further obtains body information of the patient; and
the measurement unit derives the diagnosis information using both the group feature value and the body information.

2. The medical image-based tumor detection and diagnostic device of claim 1, wherein the preprocessing unit aligns a direction of the obtained medical image, corrects signal deflection in the obtained medical image to implement uniformity in the obtained medical image, and removes a region in the obtained medical image except for the tumor region which is a target.

3. The medical image-based tumor detection and diagnostic device of claim 1, wherein the deep neural network-based deep learning technique uses a DSC (depth-wise separable convolution) block capable of reducing the number of variables and the number of arithmetic operations by changing at least one of an arithmetic operation order and an arithmetic method.

4. The medical image-based tumor detection and diagnostic device of claim 3 wherein in the application of the DSC block, the deep neural network-based deep learning technique applies skip-connection to prevent a loss of information in the image inputted to the deep neural network.

5. The medical image-based tumor detection and diagnostic device of claim 1, wherein the deep neural network-based deep learning technique uses an ASPP (Atrous spatial pyramid pooling) block for performing multi-scale pooling, over a plurality of steps, on an Atrous convolution for performing a wider FOV (field of view) arithmetic operation with the same number of parameters by expanding a convolution filter.

6. The medical image-based tumor detection and diagnostic device of claim 1, wherein the deep neural network-based deep learning technique uses up-and-down sampling to obtain a plurality of features derived in accordance with a plurality of scales.

7. The medical image-based tumor detection and diagnostic device of claim 1, wherein the measurement unit predicts prognosis related to the tumor by combining clinical information and the object level information.

8. The medical image-based tumor detection and diagnostic device of claim 1, further comprising:
a storage unit configured to perform reverse processing on matrix information obtained by a grouping operation of the measurement unit so that the matrix information matches an original medical image space obtained by the input unit and then store the matrix information,
wherein the storage unit stores the grouped region and the group feature value.

9. The medical image-based tumor detection and diagnostic device of claim 1, wherein the tumor comprises brain tumor, metastatic brain cancer, lung cancer, breast cancer, liver cancer, colorectal cancer, prostate cancer, cervical cancer, and pancreatic cancer.

10. The medical image-based tumor detection and diagnostic device of claim 1, wherein the preprocessing unit preprocesses the obtained medical image in order to observe at least one of a lung calcification region and a brain white matter hyperintensity region in addition to the tumor region.

* * * * *